(12) United States Patent
Clader et al.

(10) Patent No.: US 6,689,783 B2
(45) Date of Patent: Feb. 10, 2004

(54) ARYL OXIME-PIPERAZINES USEFUL AS CCR5 ANTAGONISTS

(75) Inventors: John W. Clader, Cranford, NJ (US); Sue-Ing Y. Lin, East Hanover, NJ (US); Stuart W. Mc Combie, Caldwell, NJ (US); Pradeep B. Pushpavanam, Edison, NJ (US); Susan Vice, Mountainside, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/107,992

(22) Filed: Mar. 27, 2002

(65) Prior Publication Data

US 2003/0087912 A1 May 8, 2003

Related U.S. Application Data

(60) Provisional application No. 60/279,950, filed on Mar. 29, 2001.

(51) Int. Cl.[7] ............... A61K 31/496; C07D 401/04; C07D 401/14
(52) U.S. Cl. .................. 514/252.18; 514/252.11; 514/252.13; 544/357; 544/360; 544/364; 544/295
(58) Field of Search ................ 544/364, 360, 544/295, 357; 514/252.18, 253.13, 252.11

(56) References Cited

U.S. PATENT DOCUMENTS

| | | |
|---|---|---|
| 4,211,771 A | 7/1980 | Witkowski et al. |
| 4,530,787 A | 7/1985 | Shaked et al. |
| 4,569,790 A | 2/1986 | Koths et al. |
| 4,604,377 A | 8/1986 | Fernandes et al. |
| 4,748,234 A | 5/1988 | Dorin et al. |
| 4,949,314 A | 8/1990 | Murphree |
| RE33,653 E | 7/1991 | Mark et al. |
| 5,368,854 A | 11/1994 | Rennick |
| 5,464,933 A | 11/1995 | Bolognesi et al. |

FOREIGN PATENT DOCUMENTS

| | | |
|---|---|---|
| EP | 0142268 | 5/1985 |
| EP | 0 353 821 A | 2/1990 |
| EP | 0176299 | 3/1992 |
| WO | WO96/25171 | 8/1996 |
| WO | WO 00 66558 | 11/2000 |

OTHER PUBLICATIONS

Oppenheim et al, Arthritis Research & Therapy, vol. 4, Suppl. 3, pp. S183–S188 (2002).*
Tagat et al. Bioorganic & Medicinal Chemistry Letters, vol. 11, p. 2143–2146 (2001).*
Vandamme, A–M, *Antiviral Chemistry & Chemotherapy, 9:187* (1989) 203.
Connor, et al, *Virology, 206* (1995), 935–944.

* cited by examiner

*Primary Examiner*—Emily Bernhardt
(74) *Attorney, Agent, or Firm*—Palaiyur S. Kalyanaraman

(57) ABSTRACT

In one embodiment, this invention provides a novel class of aryl oxime-piperazine compounds as antagonists of the CCR5 receptor, methods of preparing such compounds, pharmaceutical compositions containing one or more of the compounds, methods of preparing pharmaceutical formulations comprising one or more such compounds, and methods of treatment, prevention or amelioration of one or more of diseases associated with the CCR5 receptor. An illustrative inventive compound is shown below:

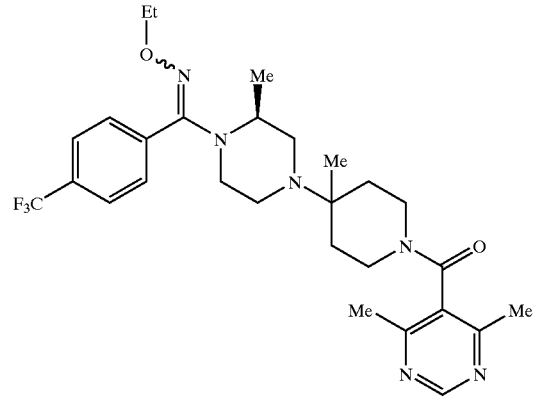

20 Claims, No Drawings

ARYL OXIME-PIPERAZINES USEFUL AS CCR5 ANTAGONISTS

This application claims priority from pending U.S>provisional patent application Ser. No. 60/279,950 filed Mar. 29, 2001.

FIELD OF THE INVENTION

The present invention relates to aryl oxime-piperazine derivatives useful as selective CCR5 antagonists, pharmaceutical compositions containing the compounds, and methods of treatment using the compounds. The invention also relates to the use of a combination of a CCR5 antagonist of this invention and one or more antiviral or other agents useful in the treatment of Human Immunodeficiency Virus (HIV). The invention further relates to the use of a CCR5 antagonist of this invention, alone or in combination with another agent, in the treatment of solid organ transplant rejection, graft v. host disease, arthritis, rheumatoid arthritis, inflammatory bowel disease, atopic dermatitis, psoriasis, asthma, allergies or multiple sclerosis.

BACKGROUND OF THE INVENTION

The global health crisis caused by HIV, the causative agent of Acquired Immunodeficiency Syndrome (AIDS), is unquestioned, and while recent advances in drug therapies have been successful in slowing the progression of AIDS, there is still a need to find a safer, more efficient, less expensive way to control the virus.

It has been reported that the CCR5 gene plays a role in resistance to HIV infection. HIV infection begins by attachment of the virus to a target cell membrane through interaction with the cellular receptor CD4 and a secondary chemokine co-receptor molecule, and proceeds by replication and dissemination of infected cells through the blood and other tissue. There are various chemokine receptors, but for macrophage-tropic HIV, believed to be the key pathogenic strain that replicates in vivo in the early stages of infection, the principal chemokine receptor required for the entry of HIV into the cell is CCR5. Therefore, interfering with the interaction between the viral receptor CCR5 and HIV can block HIV entry into the cell. The present invention relates to small molecules which are CCR5 antagonists.

CCR5 receptors have been reported to mediate cell transfer in inflammatory diseases such as arthritis, rheumatoid arthritis, atopic dermatitis, psoriasis, asthma and allergies, and inhibitors of such receptors are expected to be useful in the treatment of such diseases, and in the treatment of other inflammatory diseases or conditions such as inflammatory bowel disease, multiple sclerosis, solid organ transplant rejection and graft v. host disease.

A-M. Vandamme et al., *Antiviral Chemistry & Chemotherapy*, 9:187 (1998) 203 disclose current clinical treatments of HIV-1 infections in man including at least triple drug combinations or so-called Highly Active Anti-retroviral Therapy ("HAART"); HAART involves various combinations of nucleoside reverse transcriptase inhibitors ("NRTI"), non-nucleoside reverse transcriptase inhibitors ("NNRTI") and HIV protease inhibitors ("PI"). In compliant drug-naive patients, HAART is effective in reducing mortality and progression of HIV-1 to AIDS. However, these multidrug therapies do not eliminate HIV-1 and long-term treatment usually results in multidrug resistance. Development of new drug therapies to provide better HIV-1 treatment remains a priority.

SUMMARY OF THE INVENTION

In its many embodiments, the present invention provides a novel class of compounds as antagonists of the CCR5 receptor, methods of preparing such compounds, pharmaceutical compositions containing one or more such compounds, methods of preparing pharmaceutical formulations comprising one or more such compounds, and methods of treatment, prevention or amelioration of one or more diseases associated with the CCR5 receptor. In one embodiment, the present application discloses a compound, including enantiomers, stereoisomers, rotamers, tautomers, racemates and prodrug of said compound, and pharmaceutically acceptable salts or solvates of said compound or of said prodrug, said compound having the general structure shown in formula I:

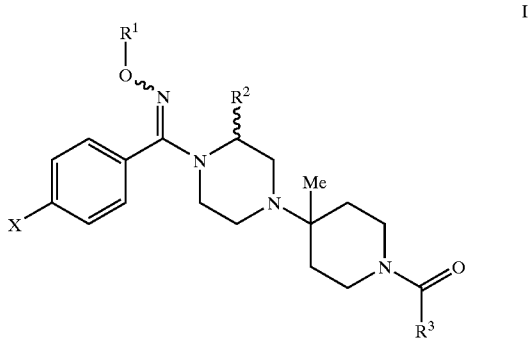

wherein:

X is-selected from the group consisting of H; F; Cl; Br; I; —$CF_3$; —$CF_3O$; —CN; $CH_3SO_2$—; and $CF_3SO_2$—;

$R^1$ is H; straight chain alkyl or a branched alkyl; fluoro-$C_1$–$C_6$ alkyl; a $C_1$–$C_6$ alkylene carrying a $C_3$–$C_7$ cycloalkyl (for example, cyclopropylmethyl);
—$CH_2CH_2OH$; —$CH_2CH_2$—O—($C_1$–$C_6$)alkyl; —$CH_2C$(O)—O—($C_1$—$C_6$)alkyl;
—$CH_2C(O)NH_2$; —$CH_2C(O)$—NH($C_1$–$C_6$)alkyl; or —$CH_2C(O)$—N(($C_1$—$C_6$)alkyl)$_2$;

$R^2$ is H; a $C_1$–$C_6$ straight chain alkyl or a branched alkyl; or a $C_2$–$C_6$ alkenyl;

$R^3$ is a $C_1$–$C_6$ straight chain alkyl or branched alkyl; phenyl substituted with $R^4$, $R^5$, $R^6$; 6-membered heteroaryl substituted with $R^4$, $R^5$, $R^6$; 6-membered heteroaryl N-oxide substituted with $R^4$, $R^5$, $R^6$; 5-membered heteroaryl substituted with $R^7$, $R^8$; naphthyl; fluorenyl; diphenylmethyl;

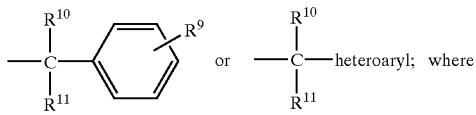

$R^4$ and $R^5$ may be the same or different and are independently selected from the group consisting of ($C_1$–$C_6$)alkyl, halogen, —$NR^{12}R^{13}$, —OH, —$CF_3$,—$OCH_3$, —O-acyl, —$OCF_3$ and —Si($CH_3$)$_3$;

$R^6$ is $R^4$; hydrogen; phenyl; —$NO_2$; —CN; —$CH_2F$; —$CHF_2$; —CHO; —CH=$NOR^{12}$; pyridyl; pyridyl N-oxide; pyrimidinyl; pyrazinyl; —N($R^{12}$)CONR$^{13}R^{14}$; —N HCONH(chloro—($C_1$–$C_6$)alkyl); —NHCONH(($C_3$–$C_{10}$)cycloalkyl($C_1$–$C_6$)alkyl); —NHCO($C_1$–$C_6$)alkyl; —NHCOCF$_3$; —NHSO$_2$N(($C_1$–$C_6$)alkyl)$_2$; —NHSO$_2$($C_1$–$C_6$)alkyl; —N(SO$_2$CF$_3$)$_2$; —N HCO$_2$($C_1$–$C_6$)alkyl); $C_3$–$C_{10}$ cycloalkyl; —$SR^{15}$; —$SOR^{15}$; —$SO_2R^{15}$;

—SO$_2$NH(C$_1$–C$_6$ alkyl); —OSO$_2$(C$_1$–C$_6$)alkyl; —OSO$_2$CF$_3$; hydroxy(C$_1$–C$_6$)alkyl; —CONR$^{12}$R$^{13}$; —CON(CH$_2$CH$_2$—O—CH$_3$)$_2$; —OCONH(C$_1$–C$_6$)alkyl; —CO$_2$R$^2$; —Si(CH$_3$)$_3$ or —B(OC(CH$_3$)$_2$)$_2$;

R$^7$ is (C$_1$–C$_6$)alkyl, —NH$_2$ or R$^9$-phenyl;

R$^9$ is 1 to 3 substituents which may be the same or different and are independently selected from the group consisting of hydrogen, (C$_1$–C$_6$) alkyl, —CF$_3$, —CO$_2$R$^{12}$, —CN, (C$_1$–C$_6$)alkoxy and halogen;

R$^{10}$ and R$^{11}$ may be the same or different and are independently selected from the group consisting of hydrogen and C$_1$–C$_6$ alkyl, or R$^{10}$ and R$^{11}$ together are a C$_2$–C$_5$ alkylene group and with the carbon to which they are attached form a spiro ring of 3 to 6 carbon atoms;

R$^{12}$, R$^{13}$ and R$^{14}$ may be the same or different and are independently selected from the group consisting of H and C$_1$–C$_6$ alkyl; and R$^{15}$ is C$_1$–C$_6$ alkyl or phenyl.

Preferred are compounds of formula I wherein R$^1$ is a C$_1$–C$_6$ straight chain alkyl or branched alkyl, with methyl and ethyl being more preferred moieties for R$^1$.

Preferred moieties for X are: halogen, —CF$_3$ and —CF$_3$O.

Preferred definition for R$^2$ is a C$_1$–C$_6$ straight chain alkyl or branched alkyl, with methyl being more preferred.

Preferred definitions for R$^3$ is 2,6-dialkylaryl or 2,6-dialkylheteroaryl, with the more preferred moieties for R$^3$ being:

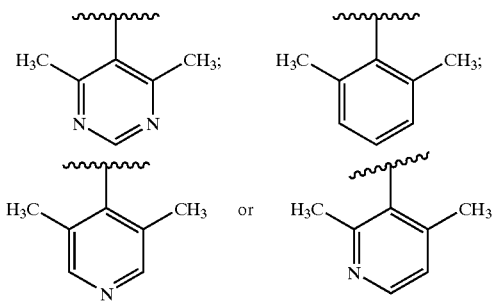

and N-oxides thereof.

Another aspect of the invention is a pharmaceutical composition for treatment of HIV comprising an effective amount of a CCR5 antagonist of formula I in combination with a pharmaceutically acceptable carrier.

One more aspect of the invention is a pharmaceutical composition for treatment of solid organ transplant rejection, graft v. host disease, arthritis, rheumatoid arthritis, inflammatory bowel disease, atopic dermatitis, psoriasis, asthma, allergies or multiple sclerosis comprising an effective amount of a CCR5 antagonist of formula I in combination with a pharmaceutically acceptable carrier.

Yet another aspect of this invention is a method of treatment of HIV comprising administering to a human in need of such treatment an effective amount of a CCR5 antagonist compound of formula I.

Another aspect of the invention is a method of treatment of solid organ transplant rejection, graft v. host disease, arthritis, rheumatoid arthritis, inflammatory bowel disease, atopic dermatitis, psoriasis, asthma, allergies or multiple sclerosis comprising administering to a human in need of such treatment an effective amount of a CCR5 antagonist compound of formula I.

Still another aspect of this invention is the use of a CCR5 antagonist of formula I of this invention in combination with one or more antiviral or other agents useful in the treatment of Human Immunodeficiency Virus for the treatment of AIDS.

Still another aspect of this invention is the use of a CCR5 antagonist of formula I of this invention in combination with one or more other agents useful in the treatment of solid organ transplant rejection, graft v. host disease, inflammatory bowel disease, rheumatoid arthritis or multiple sclerosis. The CCR5 and antiviral or other agents which are components of the combination can be administered in a single dosage form or they can be administered separately; a kit comprising separate dosage forms of the actives is also contemplated.

DETAILED DESCRIPTION OF THE INVENTION

As used herein, the following terms are used as defined below unless otherwise indicated.

Alkyl (including the alkyl portions of alkoxy, alkylamino and dialkylamino) represents straight and branched carbon chains and contains from one to six carbon atoms.

Alkenyl represents C$_2$–C$_6$ carbon chains having one or two unsaturated bonds, provided that two unsaturated bonds are not adjacent to each other.

Substituted phenyl means that the phenyl group can be substituted at any available position on the phenyl ring.

Acyl means a radical of a carboxylic acid having the formula alkyl-C(O)—, aryl-C(O)—, aralkyl-C(O)—, (C$_3$–C$_7$)cycloalkyl-C(O)—, (C$_3$–C$_7$)cycloalkyl-(C$_1$–C$_6$)alkyl-C(O)—, and heteroaryl —C(O)—, wherein alkyl and heteroaryl are as defined herein; aryl is R$^{12}$-phenyl or R$^{12}$-naphthyl; and aralkyl is aryl-(C$_1$–C$_6$)alkyl, wherein aryl is as defined above.

Heteroaryl represents cyclic aromatic groups of 5 or 6 atoms or bicyclic groups of 11 to 12 atoms having 1 or 2 heteroatoms independently selected from O, S or N, said heteroatom(s) interrupting a carbocyclic ring structure and having a sufficient number of delocalized pi electrons to provide aromatic character, provided that the rings do not contain adjacent oxygen and/or sulfur atoms. For 6-membered heteroaryl rings, carbon atoms can be substituted by alkyl or similar groups. Nitrogen atoms can form an N-oxide. All regioisomers are contemplated, e.g., 2-pyridyl, 3-pyridyl and 4-pyridyl. Typical 6-membered heteroaryl groups are pyridyl, pyrimidinyl, pyrazinyl, pyridazinyl and the N-oxides thereof. For 5-membered heteroaryl rings, carbon atoms can be substituted by alkyl or similar groups. Typical 5-membered heteroaryl rings are furyl, thienyl, pyrrolyl, thiazolyl, isothiazolyl, imidazolyl, pyrazolyl and isoxazolyl. 5-Membered rings having one heteroatom can be joined through the 2- or 3-position; 5-membered rings having two heteroatoms are preferably joined through the 4-position. Bicyclic groups typically are benzo-fused ring systems derived from the heteroaryl groups named above, e.g. quinolyl, phthalazinyl, quinazolinyl, benzofuranyl, benzothienyl and indolyl.

Halogen represents fluoro, chloro, bromo and iodo.

Fluoro(C$_1$–C$_6$)alkyl represents a straight or branched alkyl chain substituted by 1 to 5 fluoro atoms, which can be attached to the same or different carbon atoms, e.g., —CH$_2$F, —CHF$_2$, —CF$_3$, F$_3$CCH$_2$—and —CF$_2$CF$_3$.

A therapeutically effective amount of a CCR5 antagonist is an amount sufficient to lower HIV-1-RNA plasma levels.

One or more, preferably one to four, antiviral agents useful in anti-HIV-1 therapy may be used in combination with a CCR5 antagonist of the present invention. The antiviral agent or agents may be combined with the CCR5 antagonist in a single dosage form, or the CCR5 antagonist and the antiviral agent or agents may be administered simultaneously or sequentially as separate dosage forms. The antiviral agents contemplated for use in combination with the compounds of the present invention comprise nucleoside and nucleotide reverse transcriptase inhibitors, non-nucleoside reverse transcriptase inhibitors, protease inhibitors and other antiviral drugs listed below not falling within these classifications. In particular, the combinations known as HAART are contemplated for use in combination with the CCR5 antagonists of this invention.

The term "nucleoside and nucleotide reverse transcriptase inhibitors" ("NRTI"s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR tradename from Glaxo SmithKline, Research Triangle Park, N.C.; didanosine (ddl) available under the VIDEX tradename from Bristol-Myers Squibb Company, Princeton, N.J.; zalcitabine (ddC) available under the HIVID tradename from Roche Pharmaceuticals, Nutley, N.J. stavudine (d4T) available under the ZERIT trademark from Bristol-Myers Squibb Company; lamivudine (3TC) available under the EPIVIR tradename from Glaxo SmithKline; abacavir (1592U89) disclosed in WO96/30025 and available under the ZIAGEN trademark from Glaxo SmithKline; adefovir dipivoxil [bis (POM)-PMEA] available under the PREVON tradename from Gilead Sciences, Foster City, Calif.; lobucavir (BMS-180194), a nucleoside reverse transcriptase inhibitor disclosed in EP-0358154 and EP-0736533 and under development by Bristol-Myers Squibb Company; BCH-10652, a reverse transcriptase inhibitor (in the form of a racemic mixture of BCH-10618 and BCH-10619) under development by Biochem Pharma, Laval, Quebec, Canada; emitricitabine [(−)−FTC] licensed from Emory University under Emory Univ. U.S. Pat. No. 5,814,639 and under development by Triangle Pharmaceuticals, Durham, N.C.; beta-L-FD4 (also called beta-L-D4C and named beta-L-2', 3'-dicleoxy-5-fluoro-cytidene) licensed by Yale University to Vion Pharmaceuticals, New Haven, Conn.; DAPD, the purine nucleoside, (−)−beta-D-2,6,-diamino-purine dioxolane disclosed in EP 0656778 and licensed by Emory University and the University of Georgia to Triangle Pharmaceuticals; and lodenosine (FddA), 9-(2,3-dideoxy-2-fluoro-b-D-threo-pentofuranosyl)adenine, an acid stable purine-based reverse transcriptase inhibitor discovered by the NIH and under development by U.S. Bioscience Inc., West Conshohoken, Pen.

The term "non-nucleoside reverse transcriptase inhibitors" ("NNRTI"s) as used herein means non-nucleosides that inhibit the activity of HIV-1 reverse transcriptase.

Typical suitable NNRTIs include nevirapine (BI-RG-587) available under the VIRAMUNE tradename from Boehringer Ingelheim, the manufacturer for Roxane Laboratories, Columbus, Ohio; delaviradine (BHAP, U-90152) available under the RESCRIPTOR tradename from Pharmacia Corporation, Bridgewater, Bridgewater, N.J.; efavirenz (DMP-266) a benzoxazin-2-one disclosed in WO94/03440 and available under the SUSTIVA tradename from DuPont Pharmaceutical Co., Wilmington, Del.; PNU-142721, a furopyridine-thio-pyrimide under development by Pharmacia Corporation; AG-1549 (formerly Shionogi # S-1153); 5-(3,5-dichlorophenyl)-thio-4-isopropyl-1-(4-pyridyl)methyl-IH-imidazol-2-ylmethyl carbonate disclosed in WO 96/10019 and under clinical development by Agouron Pharmaceuticals, Inc., LaJolla, Calif.; MKC-442 (1-(ethoxy-methyl)-5-(1-methylethyl)-6-(phenylmethyl)-(2,4 (1H,3H)-pyrimidinedione) discovered by Mitsubishi Chemical Co. and under development by Triangle Pharmaceuticals; and (+)-calanolide A (NSC-675451) and B, coumarin derivatives disclosed in NIH U.S. Pat. No. 5,489,697, licensed to Med Chem Research, which is co-developing (+) calanolide A with Vita-Invest as an orally administrable product.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN (available from Merck) as well as nonpeptide protease inhibitors e.g., VIRACEPT (available from Agouron).

Typical suitable Pls include saquinavir (Ro 31-8959) available in hard gel capsules under the INVIRASE tradename and as soft gel capsules under the FORTOVASE tradename from Roche Pharmaceuticals, Nutley, N.J.; ritonavir (ABT-538) available under the NORVIR tradename from Abbott Laboratories, Abbott Park, Ill.; indinavir (MK-639) available under the CRIXIVAN tradename from Merck & Co., Inc; nelfnavir (AG-1343) available under the VIRACEPT tradename from Agouron Pharmaceuticals, Inc; amprenavir (141W94), tradename AGENERASE, a non-peptide protease inhibitor under development by Vertex Pharmaceuticals, Inc., Cambridge, Mass. and available from Glaxo SmithKline, Research Triangle Park under an expanded access program; lasinavir (BMS-234475) available from Bristol-Myers Squibb (originally discovered by Novartis, Basel, Switzerland (CGP-61755); DMP-450, a cyclic urea discovered by DuPont and under development by Triangle Pharmaceuticals; BMS-2322623, an azapeptide under development by Bristol-Myers Squibb as a 2nd-generation HIV-1 PI; ABT-378 under development by Abbott Laboratories; and AG-1 549 an orally active imidazole carbamate discovered by Shionogi (Shionogi #S-1153) and under development by Agouron Pharmaceuticals, Inc.

Other antiviral agents include hydroxyurea, ribavirin, IL-2, IL-12, pentafuside and Yissum Project No.11607. Hydroyurea (Droxia), a ribonucleoside triphosphate reductase inhibitor, the enzyme involved in the activation of T-cells, was discovered at the NCI and is under development by Bristol-Myers Squibb; in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33653,4530787, 4569790, 4604377, 4748234,4752585, and 4949314, and is available under the PROLEUKIN (aldesleukin) tradename from Chiron Corp., Emeryville, Calif., as a lyophilized powder for IV infusion or subcutaneous ("sc") administration upon reconstitution and dilution with water; a dose of about 1 to about 20 million IU/day, sc is preferred; a dose of about 15 million IU/day, sc is more preferred. IL-12 is disclosed in WO96/25171 and is available from Roche Pharmaceuticals, and American Home Products, Madison, N.J.; dose of about 0.5 microgram/kg/day to about 10 microgram/kg/day, sc is preferred. Pentafuside (DP-178, T-20) a 36-amino acid synthetic peptide, disclosed in U.S. Pat. No. 5,464,933 licensed from Duke University to Trimeris which is developing pentafuside in collaboration with Duke University; pentafuside acts by inhibiting fusion of HIV-1 to target membranes. Pentafuside (3–100 mg/day) is given as a continuous sc infusion or injection together with efavirenz and 2 PI's to HIV-1 positive patients refractory to a triple combination therapy; use of 100 mg/day is preferred. Yissum Project No. 11607, a synthetic protein based on the HIV-1 Vif protein, is under preclinical development by Yissum Research Development Co., Jerusalem 91042, Israel. Ribavirin, 1-β-D-ribofuranosyl-1H-1,2,4-triazole-3-carboxamide, is available from ICN Pharmaceuticals, Inc., Costa Mesa, Calif.; its manufacture and formulation are described in U.S. Pat. No. 4,211,771.

The term "anti-HIV-1 therapy" as used herein means any anti-HIV-1 drug found useful for treating HIV-1 infections in man alone, or as part of multidrug combination therapies, especially the HAART triple and quadruple combination therapies. Typical suitable known anti-HIV-1 therapies include, but are not limited to, multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART—multidrug combination therapies include:

(a) triple combination therapies such as two NRTIs and one PI; or (b) two NRTIs and one NNRTI; and (c) quadruple combination therapies such as two NRTIs, one PI and a second PI or one NNRTI. In treatment of naive patients, it is preferred to start anti-HIV-1 treatment with the triple combination therapy; the use of two NRTIs and one PI is preferred unless there is intolerance to PIs. Drug compliance is essential. The CD4$^+$ and HIV-1-RNA plasma levels should be monitored every 3–6 months. Should viral load plateau, a fourth drug, e.g., one PI or one NNRTI could be added. The table below further describes typical illustrative therapies:

ANTI-HIV-1 Multi Drug Combination Therapies
A. Triple Combination Therapies
　1. Two NRTIs[1]+one PI[2]
　2. Two NRTIs[1]+one NNRTI[3]
B. Quadruple Combination Therapies[4]
　Two NRTIs+one PI+a second PI or one NNRTI
C. Alternatives:[5]
　Two NRTI[1]
　One NRTI[5]+one PI[2]
　Two PIs[6]±one NRTI[7] or NNRTI[3]
　One PI[2]+one NRTI[7]+one NNRTI[3]
Footnotes to Table
1. One of the following: zidovudine+lamivudine; zidovudine+didanosine; stavudine+lamivudine; stavudine+didanosine; zidovudine+zalcitabine
2. Indinavir, nelfinavir, ritonavir or saquinavir soft gel capsules.
3. Nevirapine or delavirdine.
4. See A-M. Vandamne et al, Antiviral Chemistry & Chemotherapy 9:187 at p 193–197 and FIGS. 1+2.
5. Alternative regimens are for patients unable to take a recommended regimen because of compliance problems or toxicity, and for those who fail or relapse on a recommended regimen. Double nucleoside combinations may lead to HIV-resistance and clinical failure in many patients.
6. Most data obtained with saquinavir and ritonavir (each 400 mg bid).
7. Zidovudine, stavudine or didanosine.

Agents known in the treatment of rheumatoid arthritis, transplant and graft v. host disease, inflammatory bowel disease and multiple sclerosis which can be administered in combination with the CCR5 antagonists of the present invention are as follows:

solid organ transplant rejection and graft v. host disease: immune suppressants such as cyclosporine and Interleukin-10 (IL-10), tacrolimus, antilymphocyte globulin, OKT-3 antibody, and steroids;
　inflammatory bowel disease: IL-10 (see U.S. Pat. No. 5,368,854), steroids and azulfidine;
　rheumatoid arthritis: methotrexate, azathioprine, cyclophosphamide, steroids and mycophenolate mofetil;
　multiple sclerosis: interferon-beta, interferon-alpha, and steroids.

Certain CCR5 antagonist compounds of the invention may exist in different isomeric (e.g., enantiomers, diastereoisomers and atropisomers) forms. The invention contemplates all such isomers both in pure form and in admixture, including racemic mixtures.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of the invention can be made by the procedures known in the art as well as by the procedures described in the following reaction schemes and by the methods described in the examples below.

The following solvents and reagents may be referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxy-benzotriazole (HOBT); m-chloroperbenzoic acid (MCPBA); triethylamine (Et$_3$N); diethyl ether (Et$_2$O); tert-butoxy-carbonyl (BOC);

1,8-diazabicyclo[5.4.0]undec-7-ene (DBU); dimethylsulfoxide (DMSO); p-toluene sulfonic acid (p-TSA); potassium bis(trimethylsilyl)-amide (KHMDA); 4-dimethylaminopryidine (DMAP); N,N,N-diiospropylethylamine (Dipea); and 1-(3-dimethylaminopropyl)-3-ethyl carbodiimide hydrochloride (DEC). RT is room temperature.

Preparations:

Compounds of this invention are prepared using either of the following general procedures:

Method 1:

When R³ and the carbonyl group to which it is attached are derived from 4,6-dimethyl-pyrimidine-5-carboxylic acid, then the method described in Scheme 1 is used. Compound 1, prepared as described in WO-00066558, is converted to intermediate 2 by hydrogenolysis over a suitable catalyst such as palladium hydroxide and also in the presence of a hydrogen source such as hydrogen gas or ammonium formate. Compound 2 is heated in the presence of a hydroximinochloride 3 either neat or in the presence of a solvent such as dichloromethane and optionally in the presence of a base such as diethyl isopropylamine to give 4 (=I with R¹=H). Compound 4 is treated with a suitable alkylating agent such as an alkyl halide or alkyl methanesulfonate in the presence of a base such as potassium hydroxide, and preferably in a solvent such as toluene and in the presence of a phase-transfer catalyst such as tetrabutylammonium bromide to give compound I.

Scheme 1

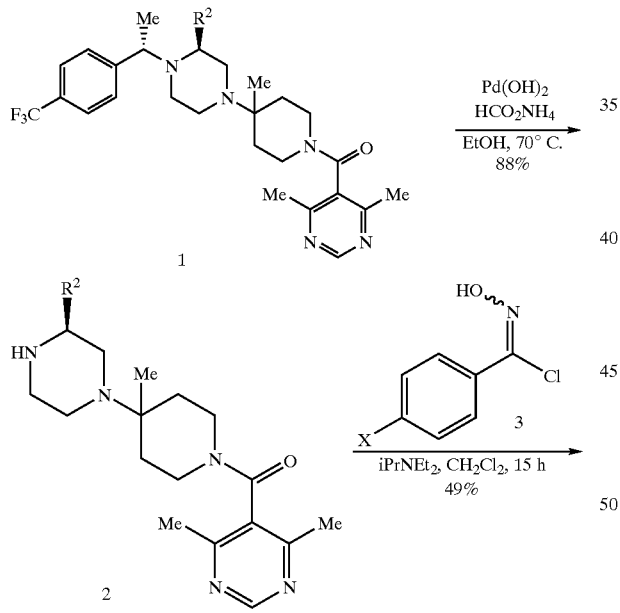

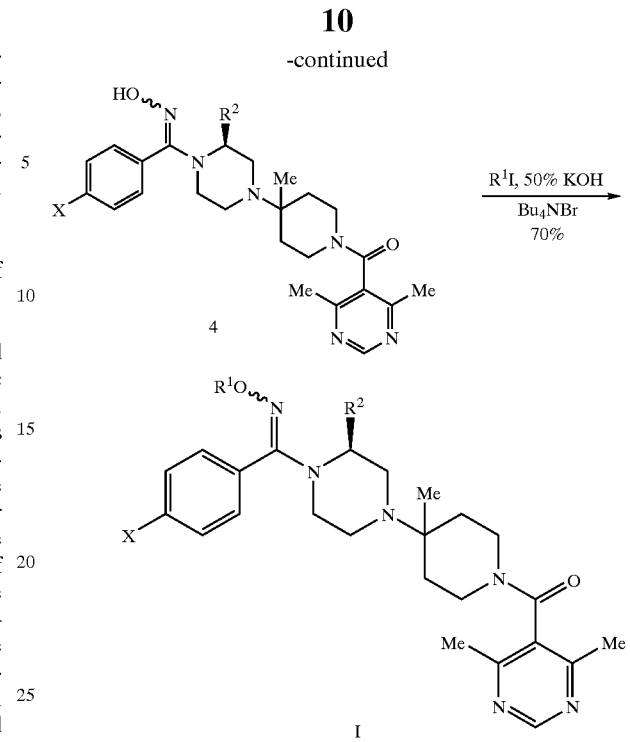

More generally, compounds I with a variety of groups R³ can be prepared as described in Scheme 2. Intermediate 5 is transformed to 6 and then optionally alkylated in a similar manner to the procedure described in Scheme 1. The Boc protecting group is removed under standard conditions to give 7, which is then coupled with a suitable carboxylic acid using standard procedures well known to those skilled in the art.

Scheme 2:

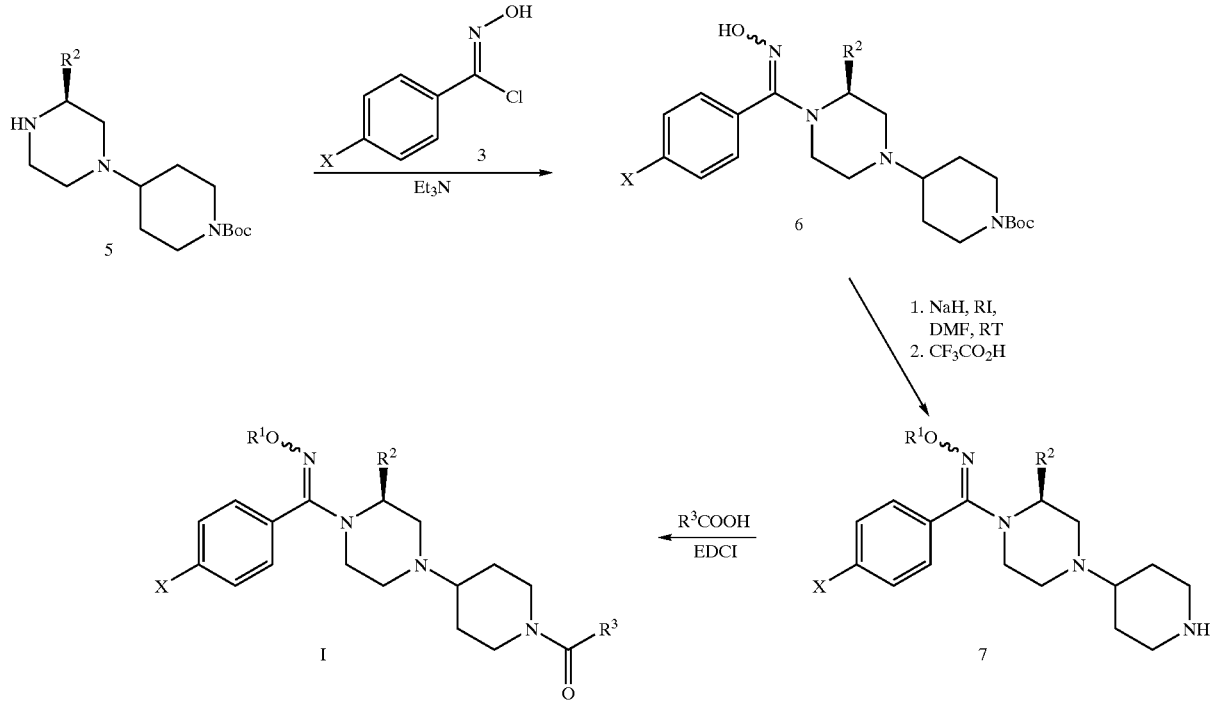

EXAMPLE 1

Preparation of 1-[(4,6-dimethyl-5-pyrimidinyl) carbonyl]-4-[4-[(ethoxyimino)[4-(trifluoromethoxy) phenyl]methyl]-3(s)-methyl-1-piperazinyl]-4-methylpiperidine (Ig)

Step 1.

To substrate 1 ($R^2$=$CH_3$) of Scheme 1(0.500 g, 9.93 mmol), prepared as described in WO-00066558, in ethanol (100 mL) was added Pd(OH)$_2$ (2.00 g, <50% wt Pd/C) followed by ammonium formate (9.39 g, 149 mmol). The reaction mixture was stirred for 23 h and then cooled to room temperature. The mixture was then filtered through a bed of celite washing with methylene chloride. The filtrate was concentrated in vacuo and taken up into aq. 1 N HCl (150 mL) and washed with ether. The aqueous layer was basified with aq. 50% NaOH and then extracted with methylene chloride. The organic layer was washed with water and brine and dried (MgSO$_4$). Filtration and evaporation of the solvent provided the amine (2.90 g, 88%).

Step 2

To the amine from step 1 (0.133 g, 0.40 mmol) in methylene chloride (1.6 mL) at room temperature was added Hunig's base (0.07 g, 0.60 mmol) and the imidoyl chloride 3 (X=CF$_3$O) (0.09 g, 0.40 mmol) in methylene chloride (0.7 mL). The reaction mixture was stirred for 17 h and then water was added. The mixture was extracted with methylene chloride. The organic layers were combined and washed with water and brine and dried (MgSO$_4$). Filtration and evaporation of the solvent in vacuo provided a foam that was purified by silica gel chromatography (6% MeOH/ethyl acetate) to afford the amidoxime 4 (X=CF$_3$O) (0.10 g, 49%).

Step3

To the amiddxime from step 2 (0.105 g, 0.19 mmol) in toluene (0.65 mL) was added aq. 50% NaOH (0.65 mL), tetrabutylammonium bromide (0.003 g, 0.05 mmol) and ethyl iodide (0.06 g, 0.39 mmol). The reaction was stirred at room temperature for 18 h and water was added. The mixture was extracted with ethyl acetate. The organic layers were combined and washed with water and brine and dried (MgSO$_4$). Filtration and evaporation of the solvent in vacuo yielded a residue that was purified by silica gel chromatography (5% methanol/ethyl acetate) to provide the 0-alkylamidoxime (0.078 g, 70%).

EXAMPLE 2

Preparation of 1-[(4,6-dimethyl-5-pyrimidinyl) carbonyl]-4-[4-[(ethoxyimino)[4-(trifluoromethyl) phenyl]methyl]-3(s)-methyl-1-piperazinyl]-4-methylpiperidine (1 h)

Step 1: A mixture of compound 5 ($R^2$=$CH_3$) of scheme 2 (0.27 gm) and triethylamine (0.15 gm) in tetrahydrofuran (5 mL) was stirred at RT and α-chloro-4-trifluoromethyl benzaldoxime 3 (X=CF$_3$) (0.218 gm) was added. After stirring for 16 hr, the mixture was evaporated, the residue partitioned between water and ethyl acetate and the organic layer dried over magnesium sulfate and evaporated. The residue was triturated with a little hexane-ether, filtered and dried to afford the crude amidoxime 6 (X=CF$_3$) (0.45 gm), mp 80-82, which was used in the next step. Step 2: The amidoxime (0.27 gm) was stirred in dimethyl formamide (5 mL) and sodium hydride (0.034 gm of 60% oil dispersion) for 10 min., them ethyl iodide (0.13 gm) added, and stirring continued for20 hr. The mixture was partitioned in ethyl acetate—water and the organic phase washed twice with water, dried over magnesium sulfate, and evaporated to give the O-ethyl compound (0.23 gm) which was treated with trifluoroacetic acid (5 mL) at room temperature for 20 hr. The mixture was evaporated, and the residue treated with excess sodium hydroxide solution, extracted with dichloromethane, dried over potassium carbonate, and evaporated to give the NH compound 7 (X=CF$_3$), suitable for use in the next step. Step 3: The NH compound (0.08 gm) was stirred at RT for 20 hr. in dichloromethane with 4,6- dimethylpyrimidine-5-carboxylic acid (0.06 gm), diisopropyl ethylamine (0.075 gm), N-hydroxybenzotriazole (0.07 gm) and EDCI (0.09 gm). The mixture was diluted with ethyl acetate, washed with aqueous sodium carbonate, dried over magnesium sulfate and evaporated, and the product was isolated by preparative silica gel plate chromatography, eluting with 7% methanol-dichloromethane to give the amide I (X=CF$_3$). This was dissolved in dichoromethane 90.3 mL) and added to excess hydrogen chloride in ether (20 mL). The precipitate was collected, washed with ether and dried. Mp 165-170.

Mass spectrum found: 533.2856. $C_{27}H_{36}N_6O_2F_3$ (MH+) requires: 533.2852.

Physical Data:

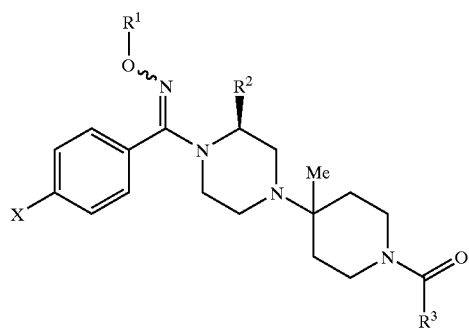

I

| X | R$^1$ | R$^2$ | R$^3$ | HRMS (M + 1) | MP(° C.) (2HCl) |
|---|---|---|---|---|---|
| A | Br | Et | Me | DMPRM | 557.2247 | 167–170 |
| B | Br | H | Me | DMPRM | 531.1910 | 182–184 |
| C | Br | Me | Me | DMPRM | 545.2067 | 175–180 |
| D | Br | H | H | DMPRM | 517.1753 | 204–206 |
| E | Br | cyclopropylmethyl | H | DMPRM | 571.2243 | 154–157 |
| F | OCF$_3$ | H | Me | DMPRM | 535.2651 | 180(decomp) |
| G | OCF$_3$ | Et | Me | DMPRM | 563.2958 | 165–169 |
| H | CF$_3$ | Et | Me | DMPRM | 533.2856 | — |
| I | Br | Me | Me | DMPYR | 544.1 (LRMS, M + 1) | — |
| J | Br | Me | H | DMPRM | See NMR data | — |

Abbreviations: DMPRM = 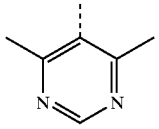

DMPYR = 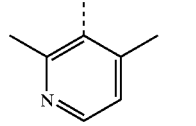

NMR data: 300 Mhz (CDCl$_3$)
Compound Ij: δ 1.1(s, 3H), 1.5–2.0(m, 4H), 2.45(s, 3H), 2.51(s, 3H), 2.4–2.6(m, 4H), 3(m, 4H), 3.3–3.5(m, 2H), 3.7(s, 3H), 7.3(d, 2H, J = 7 Hz), 7.62(d, 2H J = 7 hz), 8.95(s, 1H)

Assay:

Several types of assays can be used to determine the CCR5 inhibitory and antagonistic activity of the compounds of the invention. Some are, for example, the CCR5 Membrane Binding Assay, the HIV-1 Entry Assay, HIV-1 Replication Assay, the Calcium Flux Assay, the GTPγS Binding Assay (secondary membrane binding assay) and the Chemotaxis Assay. Compounds of this invention were evaluated for their ability to inhibit CCR5 receptor mediated viral entry using an HIV-1 entry assay, which is described below:

Replication defective HIV-1 reporter virions are generated by cotransfection of a plasmid encoding the NL4-3 strain of HIV-1 (which has been modified by mutation of the envelope gene and introduction of a luciferase reporter plasmid) along with a plasmid encoding one of several HIV-1 envelope genes as described by Connor et al, *Virology*, 206 (1995), 935–944. Following transfection of the two plasmids by calcium phosphate precipitation, the viral supernatants are harvested on day 3 and a functional viral titer determined. These stocks are then used to infect U87 cells stably expressing CD4 and the chemokine receptor CCR5 which have been preincubated with or without test compound. Infections are carried out for 2 hours at 37° C., the cells washed and media replaced with fresh media containing compound. The cells are incubated for 3 days, lysed and luciferase activity determined. Results are reported as the concentration of compound required to inhibit 50% of the luciferase activity in the control cultures.

Results of the assay on the compounds of this invention are expressed below as the concentration required to inhibit viral entry by 50% compared to control cultures. In the table, "Cmp No." stands for "Compound Number" and "nM" stands for "nanomolar."

| Cmp No | X | R$^1$ | R$^2$ | Viral Entry IC$_{50}$ (nM) |
|---|---|---|---|---|
| Ih | CF$_3$ | Et | Me | 16.46 |
| Ii | Br | Me | Me | 5.95 |
| Ij | Br | Me | H | 30 |

Pharmaceutical Compositions (formulations):

For preparing pharmaceutical compositions from the CCR5 antagonist compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences,* 18th Edition, (1990), Mack Publishing Co., Easton, Penn.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds and formulations may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 500 mg, preferably from about 25 mg to about 300 mg, more preferably from about 50 mg to about 250 mg, and most preferably from about 55 mg to about 200 mg, according to the particular application.

The actual dosage of CCR5 compound employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the CCR5 compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 100 mg/day to about 300 mg/day, preferably 150 mg/day to 250 mg/day, more preferably about 200 mg/day, in two to four divided doses.

The doses and dosage regimens of the NRTIs, NNRTIs, PIs and other agents used in combination with the CCR5 antagonists will be determined by the attending clinician in view of the approved doses and dosage regimens in the package inserts or as set forth in the protocols, taking into consideration the age, sex and condition of the patient and the severity of the condition treated.

The goal of the HIV-1 therapy of the present invention is to reduce the HIV-1-RNA viral load below the detectable limit. The "detectable limit of HIV-1-RNA" in the context of the present invention means that there are fewer than about 200 to fewer than about 50 copies of HIV-1-RNA per ml of plasma of the patient as measured by quantitative, multi-cycle reverse transcriptase PCR methodology. HIV-1-RNA is preferably measured in the present invention by the methodology of Amplicor-1 Monitor 1.5 (available from Roche Diagnsotics) or of Nuclisens HIV-1 QT-1.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound, including enantiomers, stereoisomers, rotamers, tautomers, racemates and prodrug of said compound, and pharmaceutically acceptable salts of said compound, said compound having the general structure shown in formula I:

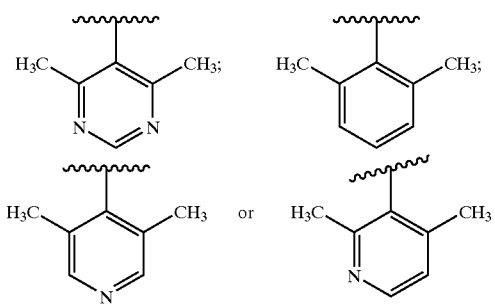

wherein:
X is-selected from the group consisting of H; F; Cl; Br; I; —CF$_3$; —CF$_3$O; —CN; CH$_3$SO$_2$—; and CF$_3$SO$_2$—;

$R^1$ is H; straight chain alkyl or a branched alkyl; fluoro-C$_1$–C$_6$ alkyl; a C$_1$–C$_6$ alkylene carrying a C$_3$–C$_7$ cycloalkyl;

—CH$_2$CH$_2$OH; —CH$_2$CH$_2$—O—(C$_1$–C$_6$)alkyl; —CH$_2$C(O)—O—(C$_1$–C$_6$)alkyl; —CH$_2$C(O)NH$_2$; —CH$_2$C(O)—NH(C$_1$–C$_6$)alkyl; or —CH$_2$C(O)—N((C$_1$–C$_6$)alkyl)$_2$;

$R^2$ is H; a C$_1$–C$_6$ straight chain alkyl or a branched alkyl; or a C$_2$–C$_6$ alkenyl;

$R^3$ is a C$_1$–C$_6$ straight chain alkyl or branched alkyl; phenyl substituted with $R^4$, $R^5$, $R^6$; pyrimidyl substituted with $R^4$, $R^5$, $R^6$; pyridyl substituted with $R^4$, $R^5$, $R^6$; pyrimidyl N-oxide substituted with $R^4$, $R^5$, $R^6$; pyridyl N-oxide substituted with $R^4$, $R^5$, $R^6$; heteroaryl substituted with $R^7$, $R^8$; naphthyl; fluorenyl; diphenyl-methyl;

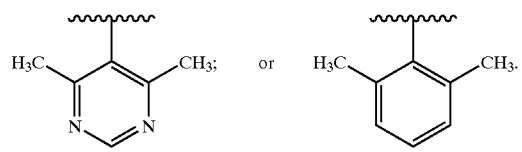

wherein heteroaryl is pyrimidyl, pyridyl, pyrimidyl N-oxide, or pyridyl N-oxide; where $R^4$ and $R^5$ may be the same or different and are independently selected from the group consisting of (C$_1$–C$_6$) alkyl, halogen, —NR$^{12}$R$^{13}$, —OH, —CF$_3$, —OCH$_3$, —O—acyl, —OCF$_3$ and —Si(CH$_3$)$_3$;

$R^6$ is $R^4$; hydrogen; phenyl; —NO$_2$; —CN; —CH$_2$F; —CHF$_2$; —CHO; —CH=NOR$^{12}$; pyridyl; pyridyl N-oxide; pyrimidinyl; pyrazinyl; —N(R$^{12}$) CONR$^{13}$R$^{14}$; —NHCONH(chloro-(C$_1$–C$_6$)alkyl); —NHCONH((C$_3$–C$_{10}$)cycloalkyl(C$_1$–C$_6$)alkyl); —NHCO(C$_1$–C$_6$)alkyl; —NHCOCF$_3$; —NHSO$_2$N((C$_1$–C$_6$)alkyl)$_2$; —NHSO$_2$(C$_1$–C$_6$)alkyl; —N(SO$_2$CF$_3$)$_2$; —NHCO$_2$(C$_1$–C$_6$)alkyl; C$_3$–C$_{10}$ cycloalkyl; —SR$^{15}$; —SOR$^{15}$; —SO$_2$R$^{15}$; —SO$_2$NH (C$_1$–C$_6$ alkyl); —OSO$_2$(C$_1$–C$_6$)alkyl; —OSO$_2$CF$_3$; hydroxy(C$_1$–C$_6$)alkyl; —CON R$^{12}$R$^{13}$; —CON (CH$_2$CH$_2$—O—CH$_3$)$_2$; —OCONH(C$_1$–C$_6$)alkyl; —CO$_2$R$^2$; —Si(CH$_3$)$_3$ or —B(OC(CH$_3$)$_2$)$_2$;

$R^7$ is (C$_1$–C$_6$)alkyl, —NH$_2$ or R$^9$-phenyl;

$R^9$ is 1 to 3 substituents which may be the same or different and are independently selected from the group consisting of hydrogen, (C$_1$–C$_6$) alkyl, —CF$_3$, —CO$_2$R$^{12}$, —CN, (C$_1$–C$_6$)alkoxy and halogen;

$R^{10}$ and $R^{11}$ may be the same or different and are independently selected from the group consisting of hydrogen and $C_1$–$C_6$ alkyl, or $R^{10}$ and $R^{11}$ together are a $C_2$–$C_5$ alkylene group and with the carbon to which they are attached form a spiro ring of 3 to 6 carbon atoms;

$R^{12}$, $R^{13}$ and $R^{14}$ may be the same or different and are independently selected from the group consisting of H and $C_1$–$C_6$ alkyl; and $R^{15}$ is $C_1$–$C_6$ alkyl or phenyl.

2. The compound of claim 1 wherein X is selected from the group consisting of F; Cl; Br; I; —$CF_3$; and —$CF_3O$.

3. The compound of claim 2, wherein X is Br, —$CF_3$ or —$CF_3O$.

4. The compound of claim 1 wherein $R^1$ is selected from the group consisting of H; a $C_1$–$C_6$ straight chain alkyl or a branched alkyl; and a $C_1$-$C_6$ alkylene carrying a $C_3$–$C_7$ cycloalkyl.

5. The compound of claim 1, wherein $R^1$ is H; methyl; ethyl or the moiety:

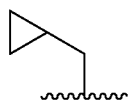

6. The compound of claim 1, wherein $R^2$ is H; a $C_1$–$C_6$ straight chain alkyl.

7. The compound of claim 6, wherein $R^2$ is H; methyl or ethyl.

8. The compound of claim 1, wherein $R^3$ is selected from the group consisting of a $C_1$–$C_6$ straight chain alkyl or branched alkyl; a phenyl substituted with 1-3 $C_1$–$C_6$ straight chain alkyl or branched alkyl; a pyrimidyl substituted with 1-3 $C_1$–$C_6$ straight chain alkyl or branched alkyl; a pyridyl substituted with 1-3 $C_1$–$C_6$ straight chain alkyl or branched alkyl; a pyrimidyl N-oxide substituted with 1-3 $C_1$–$C_6$ straight chain alkyl or branched alkyl; and a pyridyl N-oxide substituted with 1-3 $C_1$–$C_6$ straight chain alkyl or branched alkyl.

9. The compound of claim 8, wherein $R^3$ is selected from the group consisting of a phenyl substituted with two $C_1$–$C_6$ straight chain alkyls; a pyrimidyl substituted with two $C_1$–$C_6$ straight chain alkyls; a pyridyl substituted with two $C_1$–$C_6$ straight chain alkyls; a pyrimidyl N-oxide substituted with two $C_1$–$C_6$ straight chain alkyls; and a pyridyl N-oxide substituted with two $C_1$–$C_6$ straight chain alkyls.

10. The compound of claim 9, wherein $R^3$ is selected from the group consisting of the moieties:

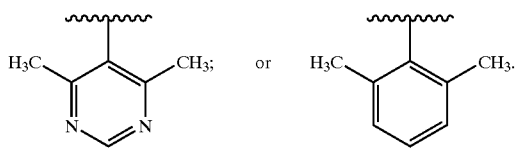

and N-oxides thereof.

11. The compound of claim 1, wherein X is Br, —$CF_3$ or —$CF_3O$; $R^1$ is H; methyl; or ethyl; $R^2$ is H; or methyl; and $R^3$ is:

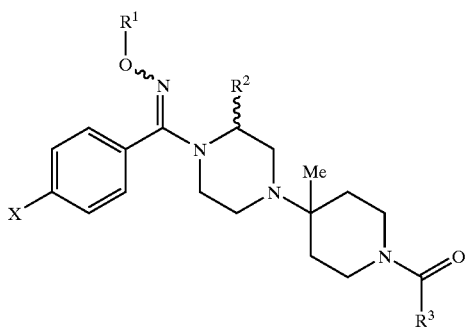

12. A compound selected from the group consisting of those represented by the formula:

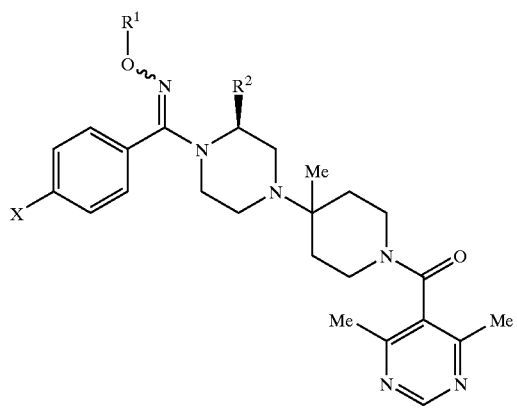

where X, $R^1$ and $R^2$ are defined in the table below:

| X | $R^1$ | $R^2$ |
|---|---|---|
| Br | Et | Me |
| Br | H | Me |
| Br | Me | Me |
| Br | H | H |
| Br | (cyclopropylmethyl) | H |
| $OCF_3$ | H | Me |
| $OCF_3$ | Et | Me |
| $CF_3$ | Et | Me |
| Br | Me | Me |
| Br | Me | H |

13. A compound selected from the group consisting of the following:

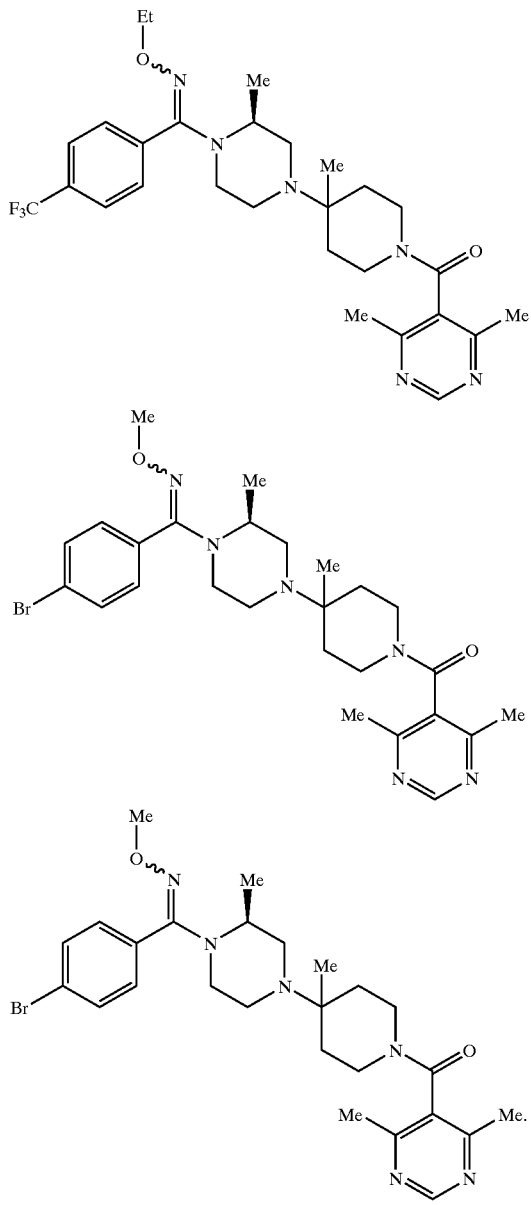

14. A pharmaceutical composition comprising an effective amount of a CCR5 antagonist of claim 1 in combination with a pharmaceutically acceptable carrier.

15. A method of treating Human Immunodeficiency Virus comprising administering to a human in need of such treatment a therapeutically effective amount of a CCR5 antagonist of claim 1.

16. A method of treating Human Immunodeficiency Virus, solid organ transplant rejection, graft v. host disease, arthritis, rheumatoid arthritis, inflammatory bowel disease, atopic dermatitis, psoriasis, asthma, allergies or multiple sclerosis, comprising administering to a human in need of such treatment an effective amount of a CCR5 antagonist, including enantiomers, stereoisomers, rotamers, tautomers, and racemates of said antagonist, and pharmaceutically acceptable salts of said antagonist, said antagonist having the general structure shown in formula I:

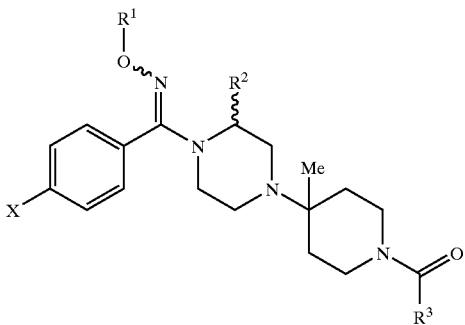

wherein:
X is selected from the group consisting of H; F; Cl; Br; I; —$CF_3$; —$CF_3O$; —CN; $CH_3SO_2$—; and $CF_3SO_2$—;

$R^1$ is H; straight chain alkyl or a branched alkyl; fluoro-$C_1$-$C_6$ alkyl; a $C_1$-$C_6$ alkylene carrying a $C_3$-$C_7$ cycloalkyl; —$CH_2CH_2OH$; —$CH_2CH_2$—O—($C_1$-$C_6$)alkyl; —$CH_2C(O)$—O—($C_1$-$C_6$)alkyl; —$CH_2C(O)NH_2$; —$CH_2C(O)$—NH($C_1$-$C_6$)alkyl; or —$CH_2C(O)$—N(($C_1$-$C_6$)alkyl)$_2$;

$R^2$ is H; a $C_1$-$C_6$ straight chain alkyl or a branched alkyl; or a $C_2$-$C_6$ alkenyl;

$R^3$ is a $C_1$-$C_6$ straight chain alkyl or branched alkyl; phenyl substituted with $R^4$, $R^5$, $R^6$; pyrimidyl substituted with $R^4$, $R^5$, $R^6$; pyridyl substituted with $R^4$, $R^5$, $R^6$; primidyl N-oxide substituted with $R^4$, $R^5$, $R^6$; primidyl N-oxide substituted with $R^4$, $R^5$, $R^6$; naphthyl; fluorenyl; diphenylmethyl;

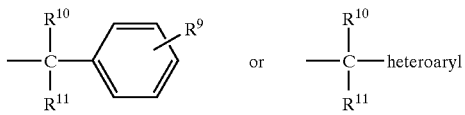

wherein heteroaryl is pyrimidyl, pyridyl, pyrimidyl N-oxide, or pyridyl N-oxide; where $R^4$ and $R^5$ may be the same or different and are independently selected from the group consisting of ($C_1$-$C_6$)alkyl, halogen, —$NR^{12}R^{13}$, —OH, —$CF_3$, —$OCH_3$, —O—acyl, —$OCF_3$ and —$Si(CH_3)_3$;

$R^6$ is $R^4$; hydrogen; phenyl; —$NO_2$; —CN; —$CH_2F$; —$CHF_2$; —CHO; —CH=$NOR^{12}$; pyridyl; pyridyl N-oxide; pyrimidinyl; pyrazinyl; —N($R^{12}$)$CONR^{13}R^{14}$; —NHCONH(chloro-($C_1$-$C_6$)alkyl); —NHCONH(($C_3$-$C_{10}$)cycloalkyl($C_1$-$C_6$)alkyl); —NHCO($C_1$-$C_6$)alkyl; —$NHCOCF_3$; —$NHSO_2N$(($C_1$-$C_6$)alkyl)$_2$; —$NHSO_2$($C_1$-$C_6$)alkyl; —N($SO_2CF_3$)$_2$; —$NHCO_2$($C_1$-$C_6$)alkyl; $C_3$-$C_{10}$ cycloalkyl; —$SR^{15}$; —$SOR^{15}$; —$SO_2R^{15}$; —$SO_2NH$($C_1$-$C_6$ alkyl); —$OSO_2$($C_1$-$C_6$)alkyl; —$OSO_2CF_3$; hydroxy($C_1$-$C_6$)alkyl; —CON $R^{12}R^{13}$; —CON($CH_2CH_2$—O—$CH_3$)$_2$; —$OCONH$($C_1$-$C_6$)alkyl; —$CO_2R^2$; —$Si(CH_3)_3$ or —$B(OC(CH_3)_2)_2$;

$R^7$ is ($C_1$-$C_6$)alkyl, —$NH_2$ or $R^9$-phenyl;

$R^9$ is 1 to 3 substituents which may be the same or different and are independently selected from the group consisting of hydrogen, ($C_1$-$C_6$) alkyl, —$CF_3$, —$CO_2R^{12}$, —CN, ($C_1$-$C_6$)alkoxy and halogen;

$R^{10}$ and $R^{11}$ may be the same or different and are independently selected from the group consisting of hydrogen and $C_1$-$C_6$ alkyl, or $R^{10}$ and $R_{11}$ together are a $C_2$-$C_5$ alkylene group and with the carbon to which they are attached form a spiro ring of 3 to 6 carbon atoms;

$R^{12}$, $R^{13}$ and $R^{14}$ may be the same or different and are independently selected from the group consisting of H and $C_1$–$C_6$ alkyl; and $R^{15}$ is $C_1$–$C_6$ alkyl or phenyl.

17. The method of claim 16 wherein X is Br, —$CF_3$ or —$CF_3O$.

18. The method of claim 16 wherein $R^1$ is H; methyl; ethyl or the moiety:

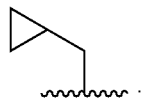

19. The method of claim 16 wherein $R^2$ is H; methyl or ethyl.

20. The method of claim 16, wherein X is Br, —$CF_3$ or —$CF_3O$; $R^1$ is H; methyl; or ethyl; $R^2$ is H; or methyl; and $R^3$ is:

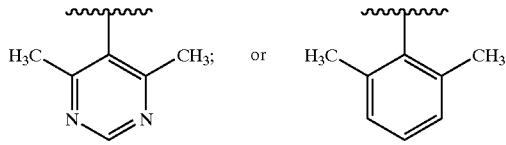

* * * * *